United States Patent
Yang et al.

(10) Patent No.: US 11,243,146 B2
(45) Date of Patent: Feb. 8, 2022

(54) METHOD FOR PRECISELY DETERMINING PROTEIN CONTENT IN EDIBLE FUNGUS

(71) Applicant: Nanjing University of Finance & Economics, Jiangsu (CN)

(72) Inventors: Wenjian Yang, Jiangsu (CN); Haoliang Pu, Jiangsu (CN); Qiuhui Hu, Jiangsu (CN); Yuanyue Wu, Jiangsu (CN); Fei Pei, Jiangsu (CN)

(73) Assignee: NANJING UNIVERSITY OF FINANCE & ECONOMICS, Jiangsu (CN)

( * ) Notice: Subject to any disclaimer, the term of this patent is extended or adjusted under 35 U.S.C. 154(b) by 408 days.

(21) Appl. No.: 16/551,100

(22) Filed: Aug. 26, 2019

(65) Prior Publication Data

US 2020/0103319 A1 Apr. 2, 2020

(30) Foreign Application Priority Data

Sep. 30, 2018 (CN) .......................... 201811154557.5

(51) Int. Cl.
| | |
|---|---|
| *G01N 1/00* | (2006.01) |
| *G01N 1/28* | (2006.01) |
| *A23L 31/00* | (2016.01) |
| *G01N 1/34* | (2006.01) |
| *G01N 1/38* | (2006.01) |
| *G01N 31/00* | (2006.01) |
| *G01N 33/02* | (2006.01) |

(52) U.S. Cl.
CPC .............. *G01N 1/286* (2013.01); *A23L 31/00* (2016.08); *G01N 1/34* (2013.01); *G01N 1/38* (2013.01); *G01N 31/002* (2013.01); *G01N 33/02* (2013.01)

(58) Field of Classification Search
None
See application file for complete search history.

(56) References Cited

U.S. PATENT DOCUMENTS

2002/0071900 A1* 6/2002 Blortz .................... A23L 31/00
426/650

* cited by examiner

*Primary Examiner* — Jyoti Nagpaul
(74) *Attorney, Agent, or Firm* — Tutunjian & Bitetto, P.C.

(57) ABSTRACT

The present invention relates to a method for precisely determining protein content in edible fungus, belonging to the technical field of food detection. The method is as follows: determining total nitrogen content in an edible fungus sample by using a Kjeldahl method; additionally taking an equal amount of sample, and washing same with acid and alkali solutions to obtain chitin residues; then determining nitrogen content in the chitin residues by using the Kjeldahl method; subtracting the nitrogen content in the chitin residues from the total nitrogen content in the sample, so as to eliminate the interference of the nitrogen content in chitin; and finally obtaining precise protein content by calculation based on a formula. The present invention provides a method for precisely determining protein content in edible fungus, and provides a method for the precise assessment of the nutrient composition and value of protein in the edible fungus.

1 Claim, 1 Drawing Sheet

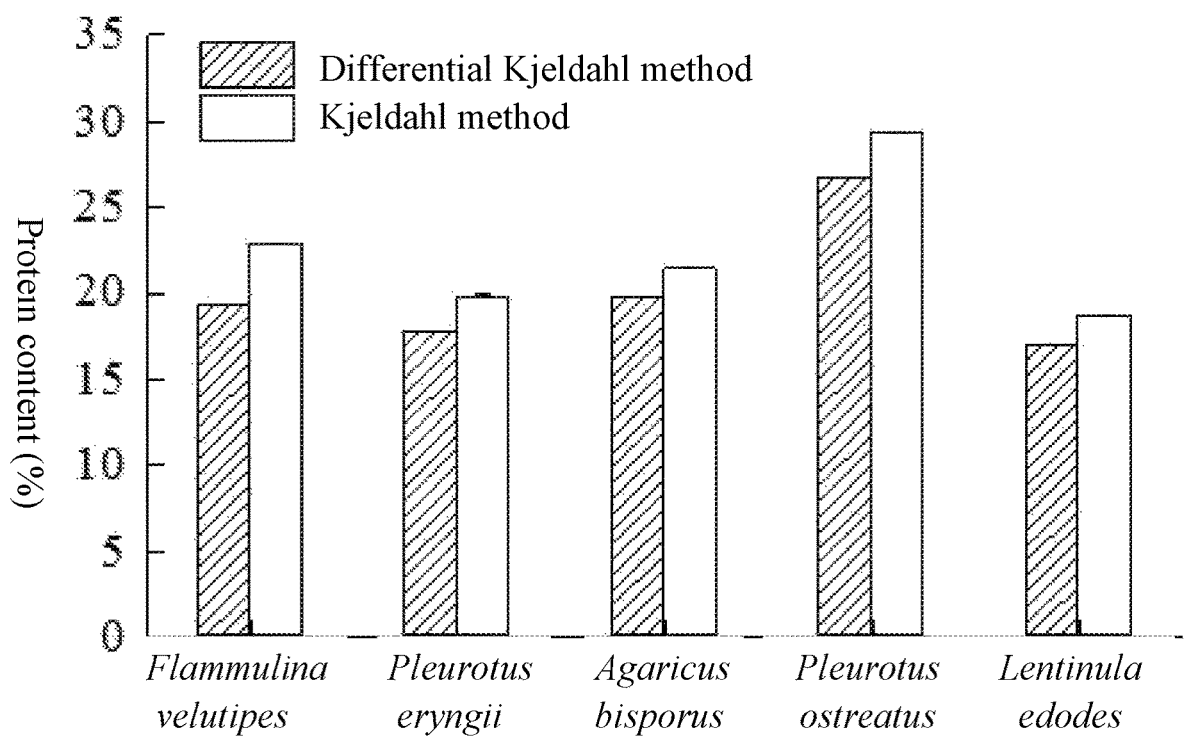

METHOD FOR PRECISELY DETERMINING PROTEIN CONTENT IN EDIBLE FUNGUS

This application claims priority to Chinese application number 201811154557.5, filed Sep. 30, 2018, with a title of METHOD FOR PRECISELY DETERMINING PROTEIN CONTENT IN EDIBLE FUNGUS. The above-mentioned patent application is incorporated herein by reference in its entirety.

TECHNICAL FIELD

The present invention relates to a method for precisely determining protein content in edible fungus, belonging to the technical field of food detection.

BACKGROUND

Edible fungus is a food with high nutrient value. Current reports show that edible fungus is rich in protein, but at present, protein content in edible fungus is mainly determined using a Kjeldahl method. Because the edible fungus contains a large amount of chitin and the chitin is a substance with high nitrogen content, using the Kjeldahl method to evaluate the protein content in the edible fungus will lead to a serious error, and a large amount of nitrogen in the chitin is mistaken for nitrogen in the protein, thus causing the determined content to be higher than the actual content. Therefore, precise determining of protein in edible fungus has far-reaching significance for the evaluation of its nutrient value.

In methods for determining protein content in foods, the Kjeldahl method is the most classical and most commonly used test method for detecting protein content at home and abroad. The results are accurate. The protein content determined by the Kjeldahl method is often taken as the standard protein content for other methods, and the application range thereof is very wide. However, the error caused by the content of non-protein nitrogen in the tested substance cannot be ignored. The chitin is a biomacromolecule formed by linearly linking β-(1,4)-2-acetylamino-2-deoxy-D-glucose residues, i.e., formed by replacing hydroxyl (—OH) on the second carbon atom of a cellulose glucopyranose residue by an acetylamino (—NHCOCH3) residue, and has high content in the edible fungus. However, the influences of the chitin on the determining of protein content have not been reported.

SUMMARY

The present invention provides a method for precisely determining protein in edible fungus, thus providing a new idea for the determining of protein content in the edible fungus, and providing technical support for the assessment of the nutrient composition and value of the protein, and quality analysis during production, sales and storage.

The technical solution used in the present invention to solve the technical problem thereof includes the steps of:

(A) treating a sample by washing the edible fungus thoroughly with running water or a cleaning machine, draining, cutting, drying at 60° C., and pulverizing with an ultrafine pulverizer to create an edible fungus powder;

(B) determining a total nitrogen content in the treated sample by accurately weighing 5.0000 g of the edible fungus powder, and determining the total nitrogen content in the sample by using a Kjeldahl method;

(C) performing chitin extraction by weighing an equal amount of edible fungus powder, adding 1 mol/L of sodium hydroxide solution at a ratio of sample to solution of 1 g:10 mL, cooking the mixture in a thermostat water bath at 95° C.-100° C. for 3 hrs, washing residue obtained by centrifugation with deionized water to neutral, adding 1 mol/L of hydrochloric acid solution to the obtained residue at a ratio of 1 g:10 mL, performing magnetic stirring at room temperature for 3 hrs, washing the residue obtained by centrifugation with deionized water to neutral, drying in an oven at 50° C. to obtain a chitin sample, and determining nitrogen content in the chitin sample by using the Kjeldahl method; and (D) calculating a precise protein content using the formula $Y(\%) = (X_1 - X_2) \times 6.25/5.0000$, wherein Y is the precise percentage of protein content of the treated sample, $X_1$ is the total nitrogen content in the sample, and $X_2$ is the total nitrogen content in the chitin.

The protein content is measured by the above method.

Beneficial Effects

The present invention creatively proposes precisely determining protein content in edible fungus by using a differential Kjeldahl method. Compared with conventional methods, the present invention is efficient, accurate, simple to operate, easy to promote, and capable of precisely determining nitrogen content of protein in edible fungus. The method for precise measurement of protein in edible fungus provided by the present invention provides technical support for the assessment of the nutrient composition and value of the protein, and quality analysis during production, sales and storage.

BRIEF DESCRIPTION OF THE DRAWINGS

FIG. 1 shows the effects of different determining methods on the determining results of protein content in edible fungus.

DETAILED DESCRIPTION

The methods and features of the present invention are described with reference to the following specific examples, and the listed examples only serve to explain the present invention, but are not intended to limit the scope of the present invention.

Embodiment 1: Determining of Protein Content in *Flammulina velutipes*

The *Flammulina velutipes* is washed thoroughly with running water or a cleaning machine, drained, cut, and then dried at 60° C., and pulverized with an ultrafine pulverizer; 5.0000 g of *Flammulina velutipes* powder is accurately weighed, and total nitrogen content in a sample is determined by using a Kjeldahl method; an equal amount of sample powder is additionally weighed, 1 mol/L of sodium hydroxide solution is added at a ratio of sample to solution of 1 g:10 mL, the mixture is cooked in a thermostat water bath at 95° C. or above for 3 h, the residue obtained by centrifugation is washed with deionized water to neutral, 1 mol/L of hydrochloric acid solution is then added to the obtained residue at a ratio of 1 g:10 mL, magnetic stirring is performed at room temperature for 3 h, the residue obtained by centrifugation is washed with deionized water to neutral and dried in an oven at 50° C. to obtain a chitin sample, and nitrogen content in the chitin sample is determined by using the Kjeldahl method; and protein content in the *Flammulina velutipes* is calculated according to a formula: Y (%)=($X_1$−$X_2$)×6.25/5.0000, where Y is the precise protein content of the sample, $X_1$ is the total nitrogen content in the sample, and $X_2$ is the total nitrogen content in chitin.

Embodiment 2: Determining of Protein Content in *Pleurotus eryngii*

The steps of the determining of the protein content in the *Pleurotus eryngii* in this embodiment are the same as those in Embodiment 1, except that the sample is changed into the *Pleurotus eryngii*.

Embodiment 3: Determining of Protein Content in *Agaricus bisporus*

The steps of the determining of the protein content in the *Agaricus bisporus* in this embodiment are the same as those in Embodiment 1, except that the sample is changed into the *Agaricus bisporus*.

Embodiment 4: Determining of Protein Content in *Pleurotus ostreatus*

The steps of the determining of the protein content in the *Pleurotus ostreatus* in this embodiment are the same as those in Embodiment 1, except that the sample is changed into the *Pleurotus ostreatus*.

Embodiment 5: Determining of Protein Content in *Lentinula edodes*

The steps of the determining of the protein content in the *Lentinula edodes* in this embodiment are the same as those in Embodiment 1, except that the sample is changed into the *Lentinula edodes*.

What is claimed is:

1. A method for precisely determining protein content in edible fungus, comprising:
    (A) treating a sample by washing the edible fungus thoroughly with running water or a cleaning machine, draining, cutting, drying at 60° C., and pulverizing with an ultrafine pulverizer to create an edible fungus powder;
    (B) determining a total nitrogen content in the treated sample by accurately weighing 5.0000 g of the edible fungus powder, and determining the total nitrogen content in the sample by using a Kjeldahl method;
    (C) performing chitin extraction by weighing an equal amount of edible fungus powder, adding 1 mol/L of sodium hydroxide solution at a ratio of sample to solution of 1 g:10 mL, cooking the mixture in a thermostat water bath at 95° C.-100° C. for 3 hrs, washing residue obtained by centrifugation with deionized water to neutral, adding 1 mol/L of hydrochloric acid solution to the obtained residue at a ratio of 1 g:10 mL, performing magnetic stirring at room temperature for 3 hrs, washing the residue obtained by centrifugation with deionized water to neutral, drying in an oven at 50° C. to obtain a chitin sample, and determining nitrogen content in the chitin sample by using the Kjeldahl method; and
    (D) calculating a precise protein content using the formula $$Y(\%)=(X_1-X_2)\times 6.25/5.0000,$$

wherein Y is the precise percentage of protein content of the treated sample, $X_1$ is the total nitrogen content in the sample, and $X_2$ is the total nitrogen content in the chitin.

* * * * *